United States Patent
Benesh

(10) Patent No.: US 9,345,854 B2
(45) Date of Patent: May 24, 2016

(54) DISTAL SHIELD FOR PACKAGED GUIDEWIRE

(71) Applicant: Lake Region Manufacturing, Inc., Chaska, MN (US)

(72) Inventor: Rick Benesh, Eden Prairie, MN (US)

(73) Assignee: Lake Region Manufacturing, Inc., Chaska, MN (US)

( * ) Notice: Subject to any disclaimer, the term of this patent is extended or adjusted under 35 U.S.C. 154(b) by 0 days.

(21) Appl. No.: 13/685,009

(22) Filed: Nov. 26, 2012

(65) Prior Publication Data

US 2014/0144798 A1     May 29, 2014

(51) Int. Cl.
*A61M 25/00* (2006.01)
*B65D 73/00* (2006.01)
*A61M 25/09* (2006.01)

(52) U.S. Cl.
CPC ......... *A61M 25/002* (2013.01); *B65D 73/0021* (2013.01); *A61M 25/09* (2013.01)

(58) Field of Classification Search
CPC .. A61B 19/026; A61B 19/02; A61B 17/0482; A61M 25/002; A61M 25/09; B65D 85/04
USPC ........ 206/364, 571, 363, 36.3, 438, 370, 389, 206/303, 53; 24/16 R, 16 PB
See application file for complete search history.

(56) References Cited

U.S. PATENT DOCUMENTS

| | | | | |
|---|---|---|---|---|
| 3,633,758 | A * | 1/1972 | Morse et al. | 211/85.13 |
| 3,952,873 | A * | 4/1976 | Pampuch et al. | 206/528 |
| 3,973,556 | A | 8/1976 | Fleischhacker et al. | |
| 4,262,800 | A * | 4/1981 | Nethercutt | 206/364 |
| 4,332,322 | A * | 6/1982 | Jaeschke et al. | 206/364 |
| 4,538,622 | A | 9/1985 | Samson et al. | |
| 4,545,390 | A | 10/1985 | Leary | |
| 5,133,454 | A * | 7/1992 | Hammer | 206/364 |
| 5,279,573 | A | 1/1994 | Klosterman | |
| 5,309,604 | A * | 5/1994 | Poulsen | 24/16 R |
| 5,323,992 | A * | 6/1994 | Sifers et al. | 248/205.3 |
| 5,366,444 | A | 11/1994 | Martin | |
| 5,417,707 | A | 5/1995 | Parkola | |
| 5,738,213 | A | 4/1998 | Whiting et al. | |
| 5,848,691 | A * | 12/1998 | Morris et al. | 206/364 |
| 6,039,722 | A | 3/2000 | Greive | |
| 6,047,826 | A * | 4/2000 | Kalinski et al. | 206/365 |
| 6,053,313 | A * | 4/2000 | Farrell et al. | 206/364 |
| 6,059,484 | A | 5/2000 | Greive | |
| 6,139,540 | A | 10/2000 | Rost et al. | |
| 6,224,585 | B1 | 5/2001 | Pfeiffer | |
| 6,231,564 | B1 | 5/2001 | Gambale | |
| 6,485,481 | B1 | 11/2002 | Pfeiffer | |
| 6,994,213 | B2 * | 2/2006 | Giard et al. | 206/363 |
| 7,234,597 | B2 * | 6/2007 | Rowe et al. | 206/438 |
| 7,357,787 | B2 | 4/2008 | Moss | |
| 7,434,687 | B2 * | 10/2008 | Itou et al. | 206/370 |
| 7,455,660 | B2 | 11/2008 | Schweikert et al. | |
| 7,549,270 | B2 * | 6/2009 | Rowe et al. | 53/430 |
| 7,714,217 | B2 | 5/2010 | Nesbitt | |
| 7,803,142 | B2 | 9/2010 | Longson et al. | |
| 7,811,623 | B2 | 10/2010 | Nesbitt | |
| 7,857,770 | B2 | 12/2010 | Raulerson et al. | |

(Continued)

*Primary Examiner* — Steven A. Reynolds
(74) *Attorney, Agent, or Firm* — Whyte Hirschboeck Dudek; Grady Frenchick; Michael F. Scalise

(57) ABSTRACT

A distal tip protector, protection shield, or packaging insert to protect the distal segment of a guidewire projecting from a guidewire carrier.

20 Claims, 6 Drawing Sheets

(56) References Cited

U.S. PATENT DOCUMENTS

| | | |
|---|---|---|
| 7,923,617 B2 | 4/2011 | Nesbitt |
| D637,891 S | 5/2011 | Chikiri |
| 7,963,947 B2 | 6/2011 | Kurth et al. |
| 7,993,329 B2 | 8/2011 | Howell et al. |
| 8,048,471 B2 | 11/2011 | Nesbitt |
| 8,240,468 B2 * | 8/2012 | Wilkinson et al. ............ 206/364 |
| 2002/0190166 A1 * | 12/2002 | Bagdi ............................ 248/71 |
| 2004/0055919 A1 * | 3/2004 | Rowe et al. .................. 206/438 |
| 2004/0187438 A1 * | 9/2004 | Clarke et al. .................... 53/400 |
| 2004/0243214 A1 * | 12/2004 | Farrell et al. ................. 623/1.11 |
| 2006/0011501 A1 * | 1/2006 | Itou et al. ...................... 206/370 |
| 2006/0278547 A1 * | 12/2006 | Rowe et al. ................... 206/364 |
| 2008/0023346 A1 * | 1/2008 | Vonderwalde ............... 206/210 |
| 2010/0264050 A1 * | 10/2010 | Clarke et al. ................. 206/438 |
| 2012/0172846 A1 * | 7/2012 | Nakamoto et al. ........... 604/533 |
| 2012/0181193 A1 * | 7/2012 | Wu ............................... 206/204 |
| 2012/0199704 A1 * | 8/2012 | Taylor ......................... 248/74.1 |
| 2012/0261290 A1 * | 10/2012 | Limjaroen et al. ............ 206/364 |

* cited by examiner

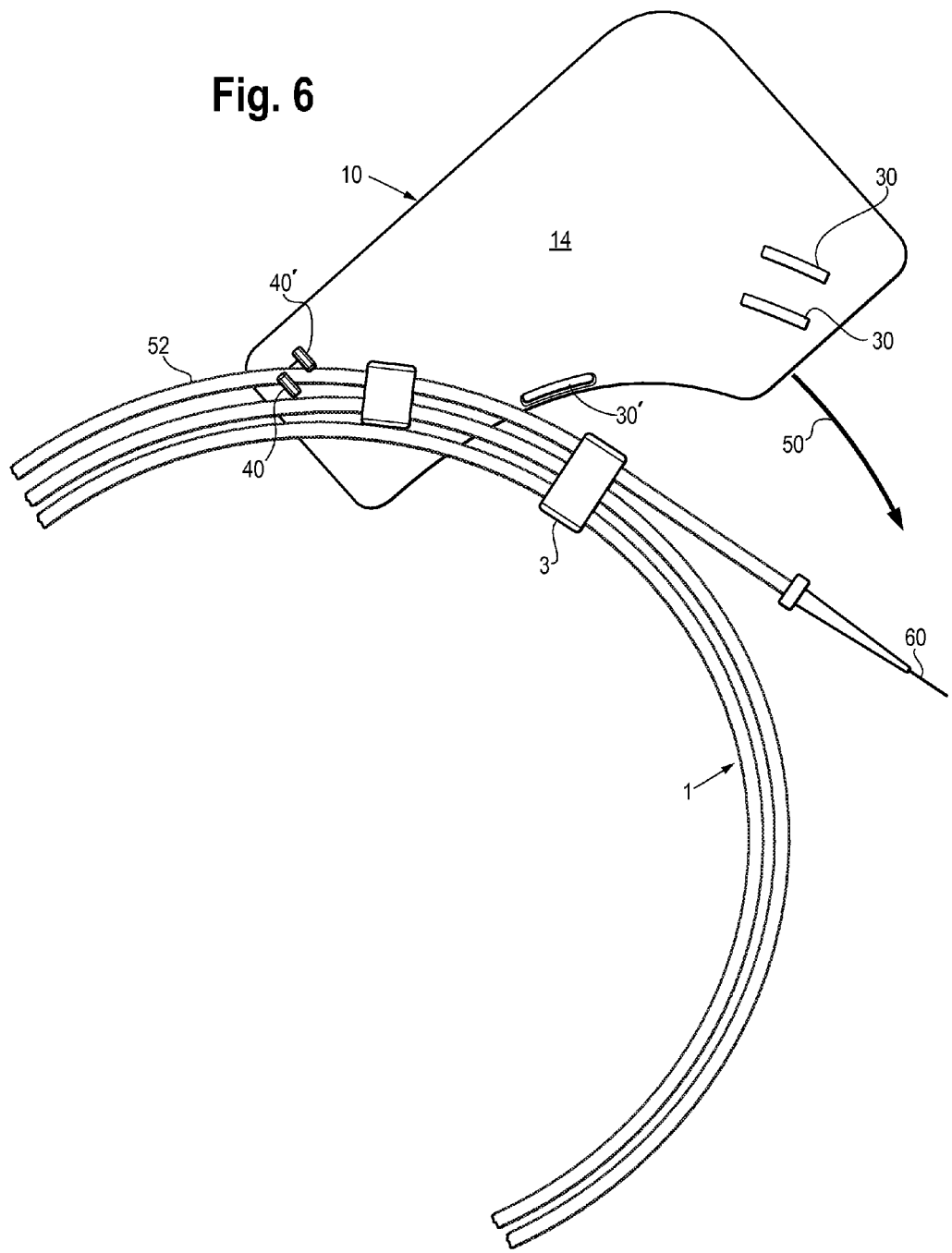

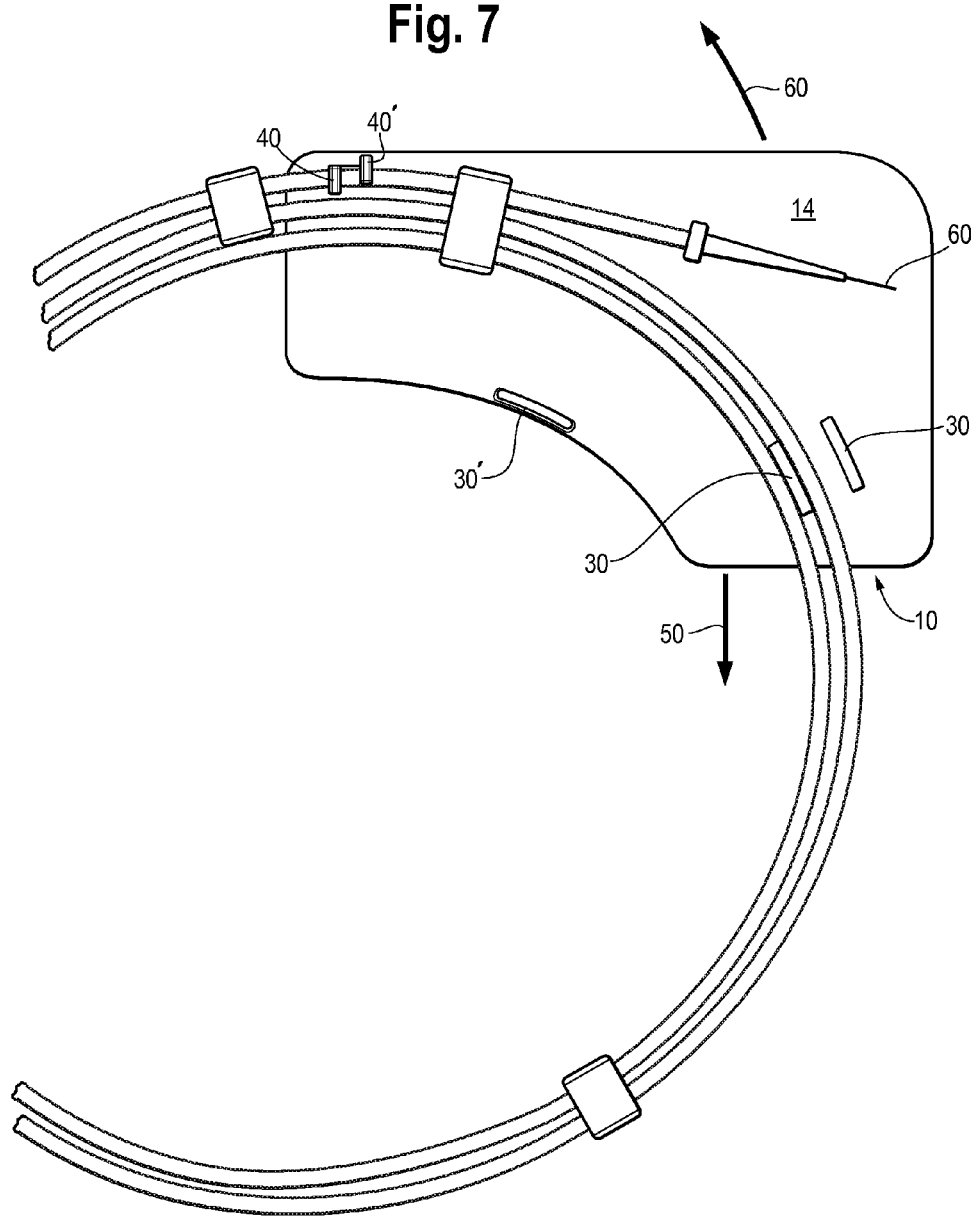

DISTAL SHIELD FOR PACKAGED GUIDEWIRE

BACKGROUND OF THE INVENTION

This invention relates to devices, or apparatuses for transporting, storing and dispensing wire from substantially cylindrical or tubular containment or carrier structures. This invention also relates to wire-containing or transporting apparatuses or carriers and in particular, a carrier for guidewires having delicate extreme distal ends or tips.

Guidewires have been described in a number of patents, representative examples of which are U.S. Pat. No. 4,545,390 to Leary, U.S. Pat. No. 3,973,556 to Fleischhacker et al., and U.S. Pat. No. 4,538,622 to Samson et al. Guidewires have many different structural features and configurations depending upon the medical procedure with which they are to be used. Generally speaking, guidewires are used in the process of directing a catheter to identified locations or sites within a patient's cardiovascular or peripheral vascular system for the purpose of diagnosis or treatment. Typically, the guidewire is placed percutaneously into a patient's blood vessel and is directed to a previously identified site. A catheter selected to provide the particular medical procedure at the site then is advanced over the guidewire until the functional structure, working surface or operating portion of the catheter is located in the proximity of the previously identified site. The catheter then is utilized to accomplish the selected medical procedure. The guidewire may be withdrawn from the vascular system before, during, or after utilization of the catheter.

A typical example of the above process would be to utilize a guidewire to direct an angiographic catheter to a site of a vascular obstruction. Thereafter an angioplasty procedure, e.g., balloon angioplasty, may be carried out by means of, e.g., a balloon angioplasty catheter. Other catheters are designed to perform procedures such as application of ultrasound to an obstruction, delivery of drugs, execution of therapeutic or diagnostic procedures, or any of a number of applications of drugs, energy or other forces, generally less invasively, within the body.

The present invention is intended to be used with essentially all guidewires. However, this invention is particularly applicable to the containment, transportation, and dispensing of guidewires in a coiled tubular dispenser assembly or carrier where the extreme distal end or tip of the guidewire is of a sufficiently delicate or complicated structure to require protection from damage during handling. A guidewire tip also may be intentionally maintained outside the carrier, e.g., a J-tip or hooked guidewire where straightening and holding the "J" in a tubular carrier could reduce or inhibit its "memory" to return to a "J" configuration.

For reasons of device protection, ease of handling and dispensing, and fluid flushing, guidewires tend to be stored and transported in tubular dispenser assemblies, carriers, or containers. Generally speaking, the tubular dispenser assembly or loop of tubing will have a substantially larger inside diameter than the outside diameter of a guidewire contained therein. To utilize a guidewire contained within such an assembly in a medical procedure, the guidewire must be partially and ultimately, totally removed therefrom.

During the transportation and handling of guidewires contained within a shipping or dispenser assembly, a problem has sometimes developed in that at least the guidewire tip may migrate or emerge from the dispenser. The tip of a guidewire can be relatively structurally fragile, comprising core/coil bonds, bulbous tip (usually) and exhibiting a tendency or memory tending to curve, cf. U.S. Pat. No. 5,279,573.

Whether having a tendency to curve or not, the extreme distal tip may project from the carrier assembly. In such instances, it is desirable to protect the guidewire distal tip from being bent or otherwise damaged during shipping, storage and use.

The present invention provides an apparatus for protecting a wire, particularly a guidewire distal end extending from a tubular, elongate, or cylindrical transfer, transportation, or carrier assembly e.g., a carrier tube having where at least a partial segment of the wire or guidewire projects from the carrier at any time during its manufacture, shipping, storage, or use.

BRIEF DESCRIPTION OF THE INVENTION

Briefly, in one aspect, the present invention is a protective shield or protective packaging insert for the extreme distal end of a guidewire projecting from a carrier therefor. The insert of the invention is primarily used when the guidewire carrier and guidewire are contained within a shipping and storage envelope.

Generally a protective shield of this invention is used with a tubular guidewire carrier by itself or in conjunction with a guidewire containment apparatus such as that shown in U.S. Pat. No. 5,279,573 to Klosterman, the teaching of which is incorporated by reference herein.

Thus, a protective packaging insert of this invention comprises a substantially flat generally quadrilateral base having a carrier side and an outside. Other base shapes are within the contemplation of this invention. The carrier side of the base has thereon, upstanding or substantially perpendicularly disposed carrier engagement means. Carrier engagement means according to this invention may be of any configuration that retains the carrier, particularly its dispensing end, adjacent to the carrier side of the base so as to protect a guidewire distal tip projecting therefrom. In one embodiment carrier engagement means take the configuration of separated, L-shaped, oppositely displaced hooks, the hooks extending from the base a distance, roughly comparable to the outside diameter of the carrier. In this embodiment of the invention, the oppositely displaced hooks are separated a distance which permits one coil of the wound carrier to be mated to or "snapped" or slid to a position adjacent the base carrier side between the hooks and the carrier to be rotated into the hooks to engage the coil to be retained adjacent the base while a second coil or coils of the carrier engage optional other carrier structure coils on the base carrier side to, in essence, retain or lock the carrier adjacent thereto and to provide distal tip protection for the guidewire oppositely aligned upstanding structures, e.g., with carrier-cooperating structures such as carve outs, and grooves.

At various points in the disclosure of this invention, it is noted that the base of a protective packaging insert of this invention is said to be located "adjacent" to the guidewire carrier and in particular the extreme distal end of a guidewire projecting therefrom. "Adjacent" as used herein means sufficiently close or sufficiently proximate that any guidewire structure intended to be protected by the base during transportation, storage and utilization is so protected. Thus, "adjacent' as used herein means, in actual contact, slightly separated, in substantially parallel deployment with respect thereto, and various other special configurations and relationships to the limit of not providing the guidewire distal tip protection which is the raison d'état for this invention.

BRIEF DESCRIPTION OF THE DRAWINGS

A better understanding of the present invention as well as other objects and advantages thereof will become apparent upon consideration of the detailed description, especially when taken with the accompanying drawings wherein like numerals designate like parts throughout, and wherein:

FIG. 5 through FIG. 7 illustrate how a distal tip protector of this invention engages and attaches to a coiled guidewire carrier;

DETAILED DESCRIPTION OF THE INVENTION

Figure 1:
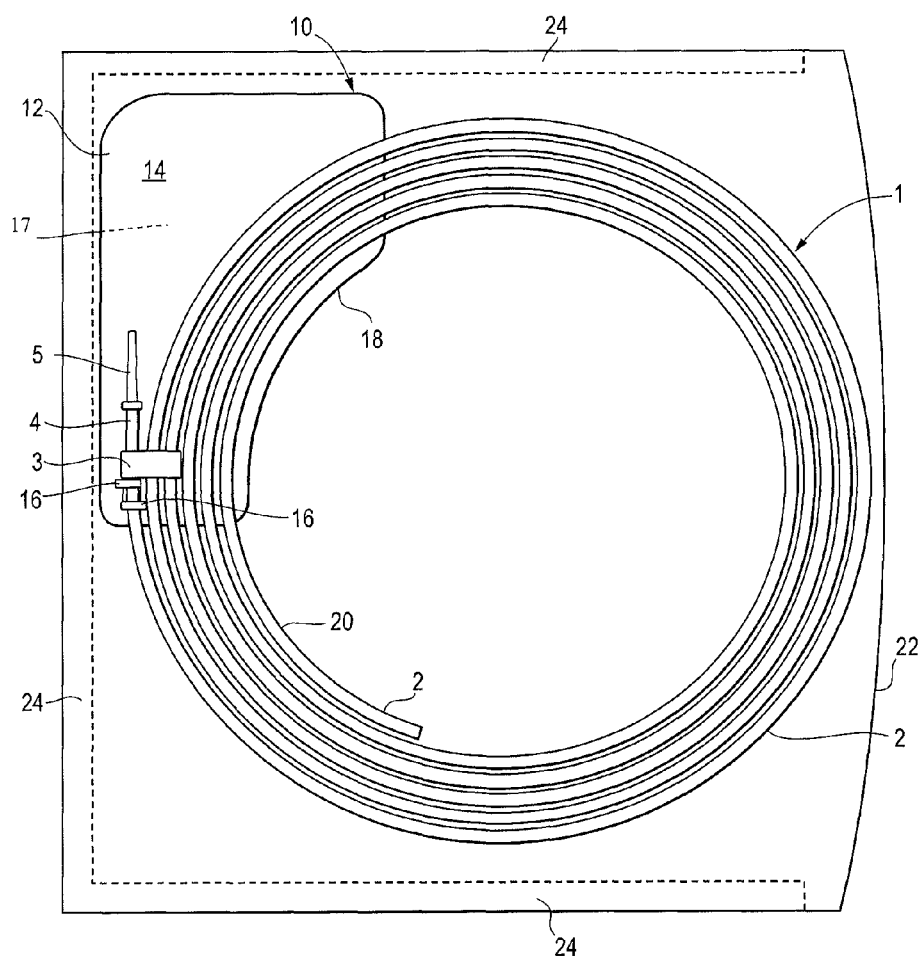
FIG. 1 is a plan view of a guidewire contained within a standard dispenser coil assembly or carrier distal tip of, the guidewire being protected by a protector of this invention.

Thus, there is shown in FIG. 1 a coiled, tubular guidewire carrier 1 having attached, coupled, or "clipped" thereto a guidewire distal tip protector 10 of this invention. In this embodiment, the carrier 1 comprises 5 or 6 coils 2 and a space clip 3 which holds the coils in a suitably flat or planar and separated arrangement so the coils can locate sufficiently closely adjacent to the tip protector 10 base 12 to be aligned and thereby retained. At the delivery end 4 of carrier 1 is a dispensing sleeve or containment tip which can be used to manage that process of dispensing a guidewire (not shown in FIG. 1) from carrier 1 c.f., U.S. Pat. No. 5,279,573.

Also shown in FIG. 1 is guidewire tip protector 10 of the invention. Tip protector 10 comprises a substantially flat base 12 having a carrier side 14 and a backside or outside 17, the dashed lead line intending to designate protector backside 17 not necessarily visible in FIG. 1. The tip protector 10 has 4 sides which may or may not be parallel. Carrier side 14 of protector 10 has carrier engagement mechanism 16 comprising oppositely disposed upwardly-protecting hooks, that are shown in greater detail in FIG. 2. Protector 10, generally is made of a formable plastic material and is about 5 inches by 3 inches in length and width. Base 12 has an arc optional or contour side 18 that generally follows the curve of the inside most carrier coil 20.

Tip protector base 12 is about ⅛ inches thick. The diameter of the entire carrier coil structure is about eight to 12 inches, its exact diameter being determined by the length of the guidewire to be transported and the circumference of the coils.

Also shown in FIG. 1 is a package or envelope 22 with which the tip protector/carrier assembly would be contained during processing, shipment, and storage prior to use. In practice envelope 22 and the protector/carrier assembly should be sterile. Envelope 22 has an adhesive field 24 (inside edge shown in dashed lines) which holds its opposite sides together. Tip protector 10 is disposed near the edge of the adhesive field and obtains support therefrom. As is shown, tip protector 10 generally fits within a corner of envelope 22.

As is discussed below (and shown in later Figures) base 12 may have optional additional alignment and support projections which provide a more controlled and stable coupling or connection between the tubular carrier 1 and protector 10.

Figure 2:
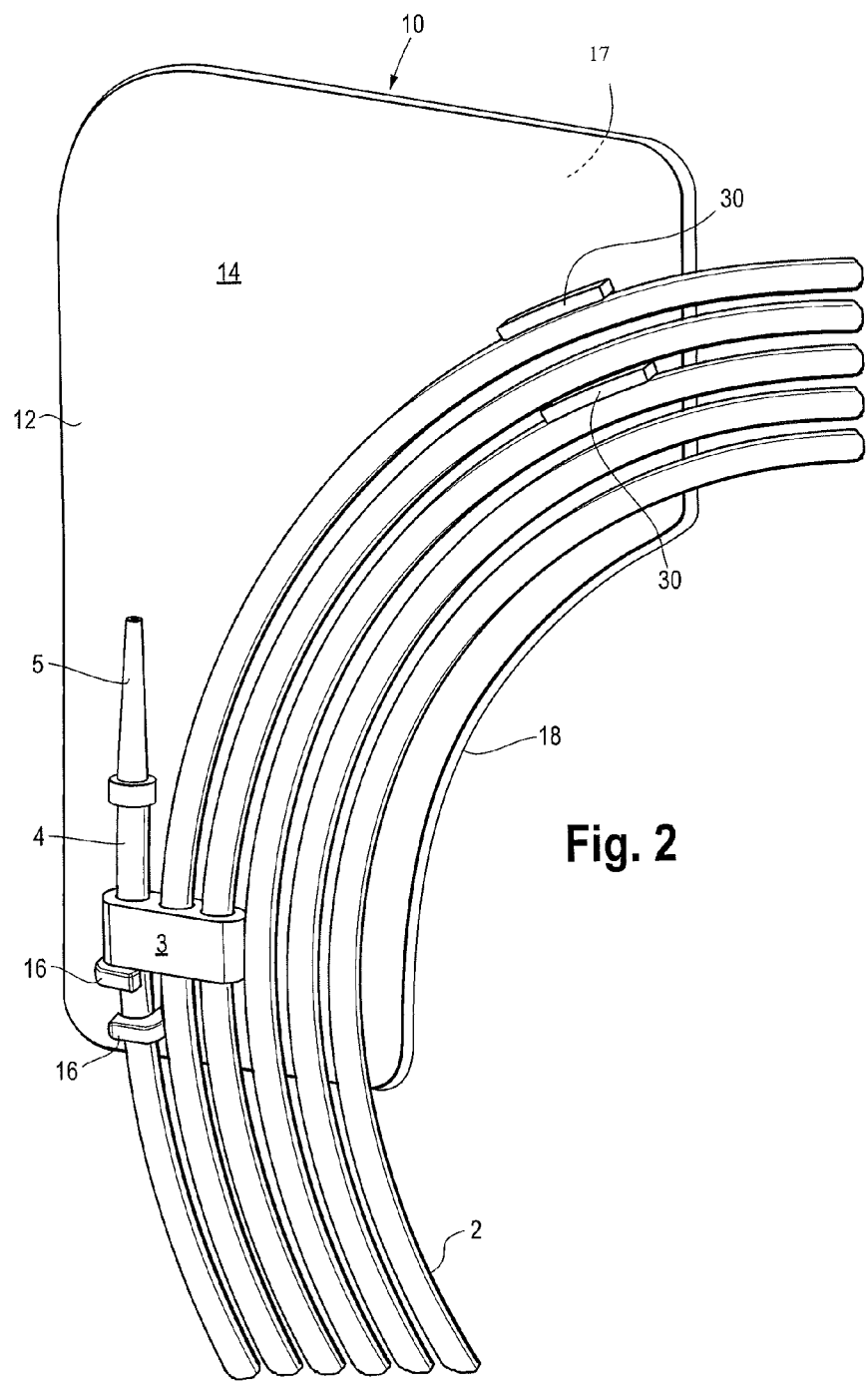
FIG. 2 is a detailed perspective view of a protector of this invention showing its interaction with a lengthy coiled guidewire carrier.

FIG. 2 shows a partial perspective view of protector 10 coupled to carrier 1. FIG. 2 shows optional upwardly projecting (from base 12 carrier side 14) arcuate tabs or retainers 30. Retainers 30 help to stabilize carrier 1 helical coil bundle adjacent carrier side 14 of protector 10 (and vice versa).

Figure 3:
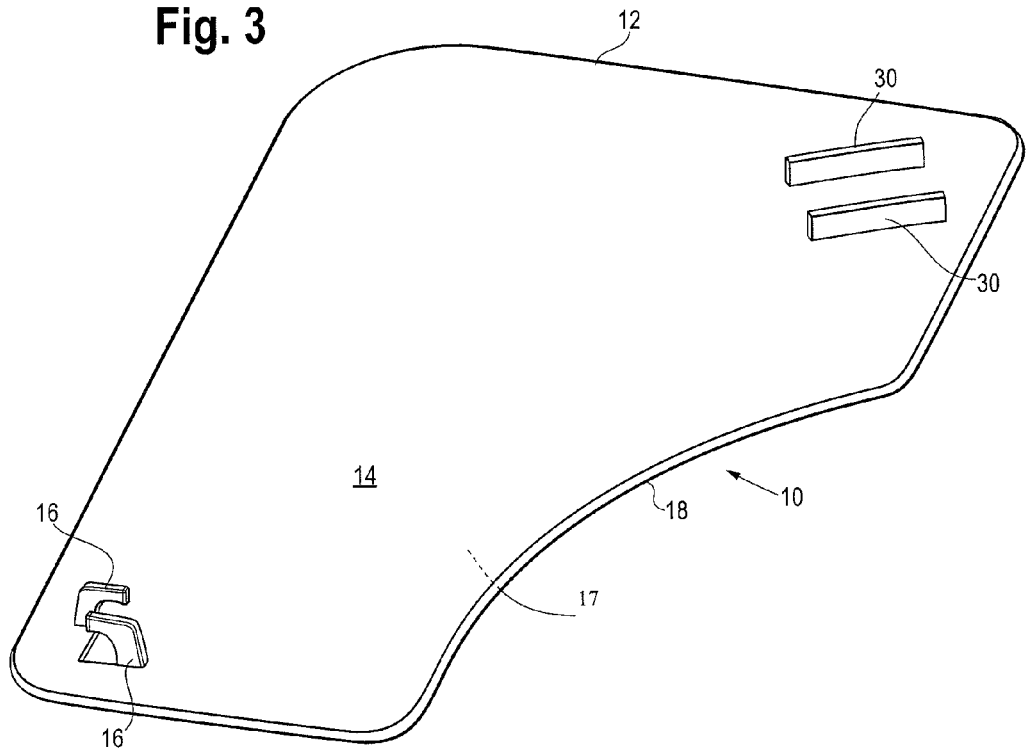
FIG. 3 is a perspective view of a distal tip protector of this invention.

FIG. 3 is a perspective view of one configuration of a tip protector 10 of this invention. Carrier engagement structure, e.g., separated, oppositely disposed hooks 16 and optional tabs 30 (which also engage one or more coils of a coiled guidewire carrier) also are shown. Numerous variation of carrier engagement structures will occur to one skilled in this art in view of this disclosure. Generally carrier engagement structure will provide either a physical engagement (e.g., hooks 16) or a frictional engagement such as tabs, teethed-structures, or tethering structures. Any such structures will project upwardly from base 12.

Figure 4:
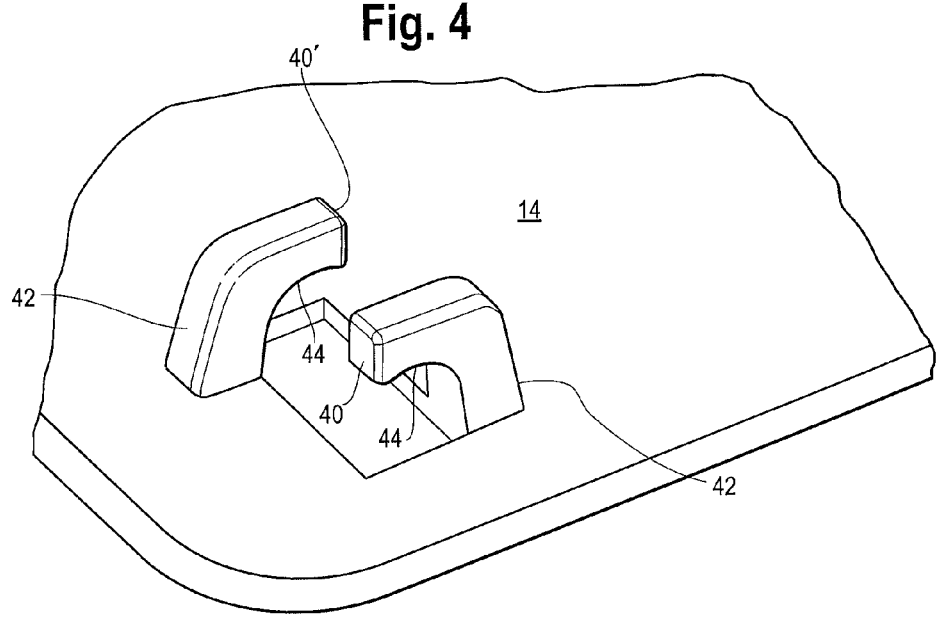
FIG. 4 is a detailed view of the oppositely disposed carrier engagement structure which projects upwardly from the distal tip protector base.

Specifically, FIG. 4 shows oppositely-disposed, upwardly projecting (from protector 10 carrier side 14) carrier engagement structure, i.e., hooks 40, 40'. Hooks 40, 40' comprise a linear portion 42 projecting approximately perpendicular from carrier side 14 of base 12 coupled to a curved portion 44. The radius of curvature of curved portion 44 approximates that of the outside tubular carrier 1.

Figure 5:
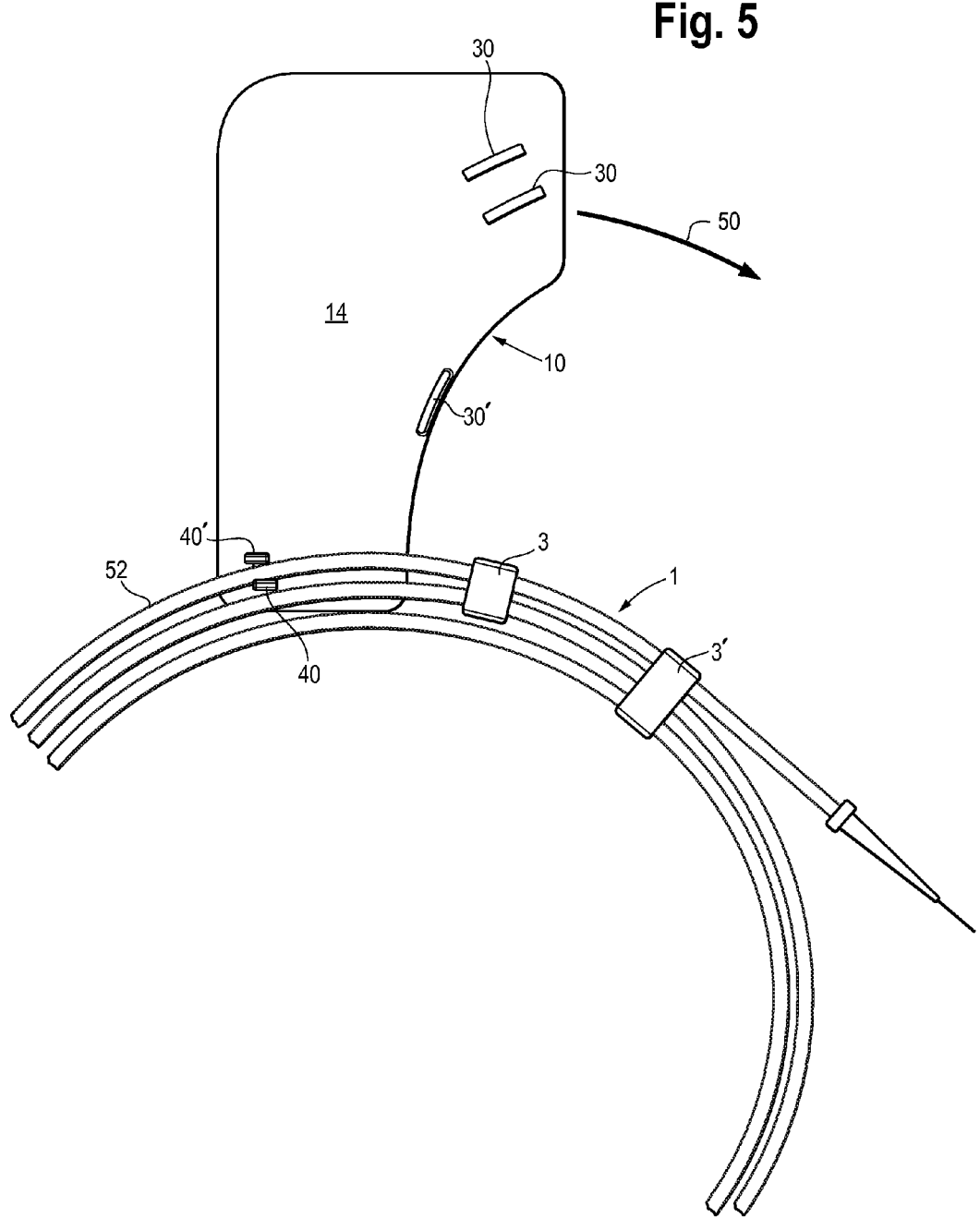

Referring now to FIGS. 5, 6, and 7 it is to be noted that hooks 40, 40' are separated by a distance that is slightly greater than the outside diameter of carrier tube 1 (best seen in FIG. 4). This arrangement permits an advantageous rotating lock procedure to engage the protector 10 to the carrier 1 as is shown in FIG. 5, one coil of carrier 1 is placed between hooks 40, 40' on carrier side 14 of protector 10. Protector 10 then is rotated clockwise (in this engagement scenario) in the direction of arrow 50.

In FIG. 6 hooks 40, 40' of proctor 10 are shown to be engaging the outside coil 52 of carrier 1 as protector 10 is rotated. As protector 10 continues to be rotated clockwise in relation to carrier 1, hooks 40, 40' engage coil 52 so that coil 52 "snaps" into engagement with hooks 40, 40' as coil 52 passes therewithin.

Thus, in FIG. 7, protector 10 is shown to be connected or coupled to carrier 1, optional engagement structure or tabs 30, adding additional support. In FIG. 7 there is shown the delicate extreme distal end of a guidewire 60. Protector 10 then provides support and protection to guidewire distal end 60 so that it is not damaged e.g., bent, during handling of the guidewire. As is noted, an overlying envelope contains the guidewire carrier/protector with the tip protector generally being deployed in one corner of the envelope. Thus, guidewire tip protection is there when it is time for the guidewire to be used during a medical procedure. Tip protector 10 is detached from carrier 1 by simply rotating tip protector 10 counterclockwise with respect thereto (i.e., in the direction of arrow 60). Protector 10 unsnaps from helical tube carrier 1, the guidewire being deployed therefrom for use in a procedure.

I claim:

1. A guidewire tip protector/carrier assembly, comprising:
   a) a tubular carrier having an outside carrier diameter and a carrier delivery end defining a carrier delivery open end;
   b) a guidewire having a distal tip, wherein the guidewire housed in the carrier is manipulatable to project its distal tip outwardly from the carrier delivery open end;
   c) a tip protector configured to protect the distal tip of the guidewire contained within the tubular carrier, wherein the protector comprises:
      i) a substantially flat base, the base having a carrier side and a back side; and
      ii) at least two hooks supported by the base, each hook comprising a projecting portion extending upwardly from the carrier side of the base to a curved hook portion, wherein the respective projecting portions are spaced apart on opposite sides of a first imaginary line by a distance that is slightly larger than the outside diameter of the carrier,
  iii) wherein the at least two hooks reside on opposite sides of a second imaginary line, the second imaginary line bisecting the first imaginary line between the two hooks, and wherein the respective curved portions of the two hooks face the second imaginary line, and
d) wherein the tubular carrier housing the guidewire is manipulatable into a position between the spaced apart at least two hooks with the carrier aligned substantially along the first imaginary line and wherein the carrier housing the guidewire is further manipulatable in a rotational manner into a contact engagement with the curved hook portions of the two hooks to thereby securely engage the carrier housing the guidewire to the protector.

2. The assembly of claim 1 further including at least two tabs upwardly projecting from the base, wherein the tabs are configured to engage and support the carrier at a location separate from that of the at least two hooks.

3. The assembly of claim 2 wherein the tabs are arcuate.

4. The assembly of claim 1 wherein the base is about ⅛ inches thick.

5. The assembly of claim 4 wherein the base is about 5 inches by 3 inches in length and width.

6. The assembly of claim 1 wherein a first radius of curvature of the curved portion of the at least two hooks is substantially similar to a second radius of curvature of an outer surface of the carrier.

7. The assembly of claim 1 further comprising a space clip configured to hold coils comprising the carrier housing the guidewire in a planar and separated configuration.

8. A guidewire tip protector/carrier assembly, comprising:
  a) a tubular carrier extending to a carrier delivery open end, wherein the carrier has an outside carrier diameter;
  b) a guidewire having a distal tip, wherein the guidewire housed in the carrier is manipulatable to project its distal tip outwardly from the carrier delivery open end;
  c) a tip protector configured to protect the distal tip of the guidewire contained within the tubular carrier, wherein the protector comprises:
    i) a substantially flat base, the base having a carrier side and a back side; and
    ii) at least two hooks supported by the base, each hook comprising a projecting portion extending upwardly from the carrier side of the base to a curved hook portion, wherein the respective projecting portions are spaced apart on opposite sides of a first imaginary line by a distance that is slightly larger than the outside diameter of the carrier,
    iii) wherein the at least two hooks reside on opposite sides of and face a second imaginary line, the second imaginary line bisecting the first imaginary line between the two hooks, and
  d) wherein the tubular carrier housing the guidewire is manipulatable into a position between the spaced apart at least two hooks with the carrier aligned substantially along the first imaginary line and wherein the carrier housing the guidewire is further manipulatable in a rotational manner into a contact engagement with the two hooks to thereby securely engage the carrier housing the guidewire to the protector.

9. The assembly of claim 8 wherein the at least two hook portions each have a curved surface facing the second imaginary line, and wherein the carrier housing the guidewire is manipulatable in the rotational manner into a contact engagement with the curved hook portions.

10. The assembly of claim 9 wherein a first radius of curvature of the curved surface of the at least two hooks is substantially similar to a second radius of curvature of an outer surface of the carrier.

11. The assembly of claim 8 further including at least two tabs upwardly projecting from the base, wherein the tabs are configured to engage and support the carrier at a location separate from that of the at least two hooks.

12. The assembly of claim 11 wherein the tabs are arcuate.

13. The assembly of claim 8 wherein the base is about ⅛ inches thick.

14. The assembly of claim 12 wherein the base is about 5 inches by 3 inches in length and width.

15. The assembly of claim 8 further comprising a space clip configured to hold coils comprising the carrier housing the guidewire in a planar and separated configuration.

16. A guidewire tip protector/carrier assembly, comprising:
  a) a tubular carrier having an outside carrier diameter and a carrier delivery end defining a carrier delivery open end;
  b) a guidewire having a distal tip, wherein the guidewire housed in the carrier is manipulatable to project its distal tip outwardly from the carrier delivery open end;
  c) a tip protector configured to protect the distal tip of the guidewire contained within the tubular carrier, wherein the protector comprises:
    i) a substantially flat base, the base having a carrier side and a back side; and
    ii) at least two hooks supported by the base, each hook comprising a projecting portion extending upwardly from the carrier side of the base to a curved hook portion, wherein the respective projecting portions are spaced apart on opposite sides of a first imaginary line by a distance that is slightly larger than the outside diameter of the carrier;
    iii) at least two tabs upwardly projecting from the base, wherein the tabs are configured to engage and support the carrier at a location separate from that of the at least two hooks,
    iv) wherein the at least two hooks reside on opposite sides of and face a second imaginary line, the second imaginary line bisecting the first imaginary line between the two hooks, and
  d) wherein the tubular carrier housing the guidewire is manipulatable into a position between the spaced apart at least two hooks with the carrier aligned substantially along the first imaginary line and wherein the carrier housing the guidewire is further manipulatable in a rotational manner into a contact engagement with the two hooks and further into contact with at least one of the at least two tabs to thereby securely engage the carrier housing the guidewire to the protector.

17. The assembly of claim 16 wherein the at least two hook portions each have a curved surface facing the second imaginary line, and wherein the carrier housing the guidewire is manipulatable in the rotational manner into a contact engagement with the curved hook portions.

18. The assembly of claim 17 wherein a first radius of curvature of the curved surface of the at least two hooks is substantially similar to a second radius of curvature of an outer surface of the carrier.

19. The assembly of claim 16 wherein the tabs are arcuate.

20. The assembly of claim 16 further comprising a space clip configured to hold coils comprising the carrier housing the guidewire in a planar and separated configuration.

* * * * *